US012765878B2

(12) United States Patent
Xu

(10) Patent No.: US 12,765,878 B2
(45) Date of Patent: Oct. 20, 2026

(54) DRIVING METHOD OF CLIP-CARTRIDGE SHAFT OF CLIP APPLICATOR AND CLIP APPLICATOR

(71) Applicant: INTOCARE MEDICAL TECHNOLOGY (SUZHOU) CO., LTD., Suzhou (CN)

(72) Inventor: Ronghua Xu, Suzhou (CN)

(73) Assignee: INTOCARE MEDICAL TECHNOLOGY (SUZHOU) CO., LTD., Jiangsu (CN)

( * ) Notice: Subject to any disclaimer, the term of this patent is extended or adjusted under 35 U.S.C. 154(b) by 824 days.

(21) Appl. No.: 18/245,882

(22) PCT Filed: Sep. 10, 2021

(86) PCT No.: PCT/CN2021/117630

§ 371 (c)(1),
(2) Date: Mar. 17, 2023

(87) PCT Pub. No.: WO2022/057732

PCT Pub. Date: Mar. 24, 2022

(65) Prior Publication Data

US 2024/0008879 A1 Jan. 11, 2024

(30) Foreign Application Priority Data

Sep. 18, 2020 (CN) ......................... 202010987800.2
Sep. 18, 2020 (CN) ......................... 202022059983.X (Continued)

(51) Int. Cl.
*A61B 17/128* (2006.01)
*A61B 17/00* (2006.01)

(52) U.S. Cl.
CPC ............................... *A61B 17/1285* (2013.01); *A61B 2017/00477* (2013.01)

(58) Field of Classification Search
CPC . A61B 17/128; A61B 17/12013; A61B 17/10; A61B 17/12009; A61B 17/0682
See application file for complete search history.

(56) References Cited

U.S. PATENT DOCUMENTS 5,111,987 A 5/1992 Moeinzadeh et al.
5,772,673 A 6/1998 Cuny et al.

(Continued)

FOREIGN PATENT DOCUMENTS

CN 212281508 U 1/2021

*Primary Examiner* — Martin T Ton
(74) *Attorney, Agent, or Firm* — McClure, Qualey & Rodack, LLP

(57) ABSTRACT

A clip-cartridge shaft of a clip applicator and a clip applicator are provided. The method includes a step of pushing the clip-cartridge shaft and a step of pulling back the clip-cartridge shaft. The step of pushing the clip-cartridge shaft includes: S12: the drive shaft drives the clip-cartridge shaft to move from the proximal-end initial position to the distal-end terminate position; after the clip-cartridge shaft leaves the proximal-end initial position, the drive shaft and the clip-cartridge shaft are locked and keep a lock state. The step of pulling back the clip-cartridge shaft includes: S21: the drive shaft drives the clip-cartridge shaft to move along the proximal-end direction, until the clip-cartridge shaft is pulled back to the proximal-end initial position and the drive shaft and the clip-cartridge shaft change to be in the connection separable under the axial external force.

10 Claims, 8 Drawing Sheets

(30) Foreign Application Priority Data

Oct. 15, 2020 (CN) ......................... 202011105221.7
Oct. 15, 2020 (CN) ......................... 202022298512.4

(56) References Cited

U.S. PATENT DOCUMENTS

| | | | | |
|---|---|---|---|---|
| 2003/0135224 | A1* | 7/2003 | Blake, III | A61B 17/1285 606/143 |
| 2014/0005693 | A1* | 1/2014 | Shelton, IV | A61B 34/30 606/143 |
| 2018/0008276 | A1* | 1/2018 | Bhatnagar | A61B 17/105 |
| 2018/0008277 | A1* | 1/2018 | Baril | A61B 17/1285 |
| 2019/0133593 | A1* | 5/2019 | P V R | A61B 17/1285 |
| 2020/0261095 | A1* | 8/2020 | Yi | A61B 17/1285 |
| 2021/0204956 | A1* | 7/2021 | Thomas | A61B 17/1285 |
| 2023/0346388 | A1* | 11/2023 | Xu | A61B 17/128 |

* cited by examiner

DRIVING METHOD OF CLIP-CARTRIDGE SHAFT OF CLIP APPLICATOR AND CLIP APPLICATOR

The present application claims priorities of Chinese Patent Application No. 202010987800.2 and No. 202022059983.X filed on Sep. 18, 2020, and claims priorities of Chinese Patent Application No. 202011105221.7 and No. 202022298512.4 filed on Oct. 15, 2020, the disclosures of the above applications are incorporated herein by reference in their entirety as part of the present application.

TECHNICAL FIELD

The present disclosure belongs to a field of medical instrument, and more particularly, to a driving method of a clip-cartridge shaft of a clip applicator and a clip applicator.

BACKGROUND

A surgical clip applicator is usually configured for clipping a tubular tissue during a surgical operation, so as to avoid exudation of fluid in the tubular tissue.

Generally, the clip applicator includes a clip-cartridge assembly and an adapter, and the clip-cartridge assembly and the adapter are in a pluggable connection. When the clip-cartridge assembly and the adapter are plugged together, a clip-cartridge shaft of the clip-cartridge assembly abuts against a drive shaft of the adapter. The clip-cartridge shaft is driven by the drive shaft to move toward a distal end, so as to feed a clip to a clip jaw, and close the clip jaw and fires the clip after the clip is feed to the clip jaw. After the clip is fired, because the clip-cartridge shaft abuts against the drive shaft, reset of the clip-cartridge shaft toward a proximal end has to only rely on a reset force of a spring, which may lead to a failed reset and further cause the clip jaw to fail to return to an open state, so that subsequent clip cannot be fired.

SUMMARY

(I) Technical Problems to be Solved

In order to solve the above-described problems of the prior art, the present disclosure provides a driving method of a clip-cartridge shaft of a clip applicator and a clip applicator that are capable of reliably driving the clip-cartridge shaft to reset.

(II) Technical Solution

In order to achieve the above-described purpose, main technical solutions of the present disclosure are as follows:

One aspect of the present disclosure provides a driving method of a clip-cartridge shaft of a clip applicator, the method comprises a step of pushing the clip-cartridge shaft and a step of pulling back the clip-cartridge shaft. The step of pushing the clip-cartridge shaft comprises: S11: a drive shaft of the clip applicator and the clip-cartridge shaft located at a proximal-end initial position of the clip-cartridge shaft form a connection separable under an axial external force; S12: the drive shaft drives the clip-cartridge shaft to move from the proximal-end initial position of the clip-cartridge shaft to a distal-end terminate position of the clip-cartridge shaft; after the clip-cartridge shaft leaves the proximal-end initial position of the clip-cartridge shaft, the drive shaft and the clip-cartridge shaft are locked and keep a lock state. The step of pulling back the clip-cartridge shaft comprises: S21: the drive shaft drives the clip-cartridge shaft to move along a proximal-end direction, until the clip-cartridge shaft is pulled back to the proximal-end initial position of the clip-cartridge shaft and the drive shaft and the clip-cartridge shaft change to be in the connection separable under the axial external force.

Preferably, in the step S11, when the clip-cartridge assembly and the adapter of the clip applicator are just connected together, the drive shaft is axially spaced apart from the clip-cartridge shaft located at the proximal-end initial position of the clip-cartridge shaft; and the drive shaft moves along a distal-end direction until the drive shaft and the clip-cartridge shaft located at the proximal-end initial position of the clip-cartridge shaft form the connection separable under the axial external force; the step of pulling back the clip-cartridge shaft further comprises: S22: the drive shaft continues to move along the proximal-end direction, so as to separate from the clip-cartridge shaft.

The other aspect of the present disclosure provides a clip applicator, the clip applicator comprises an adapter and a clip-cartridge assembly which are detachably connected together. The clip-cartridge assembly comprises a clip-cartridge shaft that moves between a proximal-end initial position of the clip-cartridge shaft and a distal-end terminate position of the clip-cartridge shaft; the adapter comprises a drive shaft located on a proximal side of the clip-cartridge shaft; when the clip-cartridge shaft is located at the proximal-end initial position of the clip-cartridge shaft, the clip-cartridge shaft and the drive shaft are in a connection separable under an axial external force; when the clip-cartridge shaft is located at the distal-end terminate position of the clip-cartridge shaft and at a position between the proximal-end initial position of the clip-cartridge shaft and the distal-end terminate position of the clip-cartridge shaft, the clip-cartridge shaft and the drive shaft are locked.

Preferably, the drive shaft moves between a proximal-end initial position of the drive shaft, a connection position, and a distal-end terminate position of the drive shaft sequentially provided from a proximal end to a distal end; when the drive shaft is located at the proximal-end initial position of the drive shaft, the drive shaft is axially spaced apart from the clip-cartridge shaft located at the proximal-end initial position of the clip-cartridge shaft; when the drive shaft is located at the connection position, the drive shaft and the clip-cartridge shaft located at the proximal-end initial position of the clip-cartridge shaft are in the connection separable under the axial external force; and when the drive shaft is located at the distal-end terminate position of the drive shaft, the clip-cartridge shaft is located at the distal-end terminate position of the clip-cartridge shaft .

Preferably, the adapter comprises a drive mechanism; the drive mechanism is connected with the drive shaft and is configured for driving the drive shaft to move along an axis direction of the drive shaft and to rotate; and lock of the drive shaft and the clip-cartridge shaft is a lock that allows synchronous axial movement and synchronous rotation of the drive shaft and the clip-cartridge shaft.

Preferably, the clip-cartridge shaft is provided with a first lock structure; the drive shaft is provided with a second lock structure; the clip-cartridge assembly is provided with a lock control structure; the lock control structure cooperates with the first lock structure and the second lock structure, so that the clip-cartridge shaft and the drive shaft are in the connection separable under the axial external force at the proximal-end initial position of the clip-cartridge shaft, and so that the clip-cartridge shaft is locked with the drive shaft at the distal-end terminate position of the clip-cartridge shaft and at the position between the proximal-end initial position of the clip-cartridge shaft and the distal-end terminate position of the clip-cartridge shaft.

Preferably, the first lock structure comprises an axial plug hole, the axial plug hole is provided at a proximal end of the clip-cartridge shaft, and the axial plug hole is in a pluggable connection with a distal end of the drive shaft; the lock control structure comprises a release surface and a limit surface located on an outer side of the clip-cartridge shaft; when the clip-cartridge shaft is located at the proximal-end initial position of the clip-cartridge shaft, the release surface and the clip-cartridge shaft are spaced apart from each other to allow a separation between the axial plug hole and the distal end of the drive shaft; when the clip-cartridge shaft is located at the distal-end terminate position of the clip-cartridge shaft and at the position between the proximal-end initial position of the clip-cartridge shaft and the distal-end terminate position of the clip-cartridge shaft, the limit surface prevents the separation between the axial plug hole and the distal end of the drive shaft.

Preferably, the first lock structure further comprises a snap member, the snap member moves radially to be inserted into the axial plug hole; when the clip-cartridge shaft is at the proximal-end initial position of the clip-cartridge shaft, a separation distance between the release surface and the clip-cartridge shaft is set such that the snap member is capable of moving to exit the axial plug hole; when the clip-cartridge shaft is located at the distal-end terminate position of the clip-cartridge shaft and at the position between the proximal-end initial position of the clip-cartridge shaft and the distal-end terminate position of the clip-cartridge shaft, the limit surface pushes the snap member to be inserted into the axial plug hole and snapped with the distal end of the drive shaft.

Preferably, the snap member comprises a plurality of groups of lock beads arranged around an axis of the clip-cartridge shaft; each group of lock beads comprises one lock bead or a plurality of lock beads arranged along a radial direction; a hole for accommodating the lock bead of the clip-cartridge shaft is a radial taper hole; a smaller end of the radial taper hole is communicated with the axial plug hole, the lock bead is capable of partially passing through the smaller end of the radial taper hole; the second lock structure comprises a plurality of lock grooves arranged at the distal end of the drive shaft in one-to-one correspondence with the plurality of groups of lock beads, and the lock bead is partially inserted into the lock groove under an action of the limit surface so as to lock with the lock groove.

Preferably, the clip-cartridge assembly further comprises a tube body, a clip-push mechanism, a firing mechanism, a first reset member and a second reset member; the clip-cartridge shaft, the clip-push mechanism and the firing mechanism are at least partially located in the tube body; during the clip-cartridge shaft moves from the proximal-end initial position of the clip-cartridge shaft to the distal-end terminate position of the clip-cartridge shaft, the clip-cartridge shaft firstly drives the clip-push mechanism to move along a distal-end direction and then drives the firing mechanism to move along the distal-end direction; the first reset member is provided between the clip-push mechanism and the clip-cartridge shaft, accumulates force during the clip-cartridge shaft moves from the proximal-end initial position of the clip-cartridge shaft to the distal-end terminate position of the clip-cartridge shaft, and drives the clip-push mechanism to reset during the clip-cartridge shaft moves from the distal-end terminate position of the clip-cartridge shaft to the proximal-end initial position of the clip-cartridge shaft; the second reset member is provided between the firing mechanism and the tube body or the clip-cartridge shaft, accumulates force during the clip-cartridge shaft moves from the proximal-end initial position of the clip-cartridge shaft to the distal-end terminate position of the clip-cartridge shaft, and drives the firing mechanism to reset during the clip-cartridge shaft moves from the distal-end terminate position of the clip-cartridge shaft to the proximal-end initial position of the clip-cartridge shaft.

(III) Advantageous Effects

The advantageous effects of the present disclosure are as follows:

According to the driving method of the clip-cartridge shaft of the clip applicator and the clip applicator provided by the present disclosure, on the one hand, at the proximal-end initial position of the clip-cartridge shaft, the clip-cartridge shaft and the drive shaft are in the connection separable under an axial external force, to facilitate the pluggable connection between the adapter and the clip-cartridge assembly; on the other hand, at positions other than the proximal-end initial position of the clip-cartridge shaft, the clip-cartridge shaft and the drive shaft are locked, so when the clip-cartridge shaft is required to reset from the distal-end terminate position of the clip-cartridge shaft to the proximal-end initial position of the clip-cartridge shaft, movement of the drive shaft along the proximal-end direction directly pulls the clip-cartridge shaft back to the proximal-end initial position of the clip-cartridge shaft, so that the clip-cartridge shaft is stably and reliably pulled back and reset, and the problem that the clip-cartridge shaft fails to fire again due to the failed reset is avoided. Meanwhile, at positions other than the initial position, because the clip-cartridge shaft and drive shaft are locked, the clip-cartridge assembly and the adapter are locked by the clip-cartridge shaft and drive shaft, so that the clip-cartridge assembly cannot be pulled out by error, which improves stability and safety of the clip applicator.

REFERENCE NUMERALS

Figure 1:
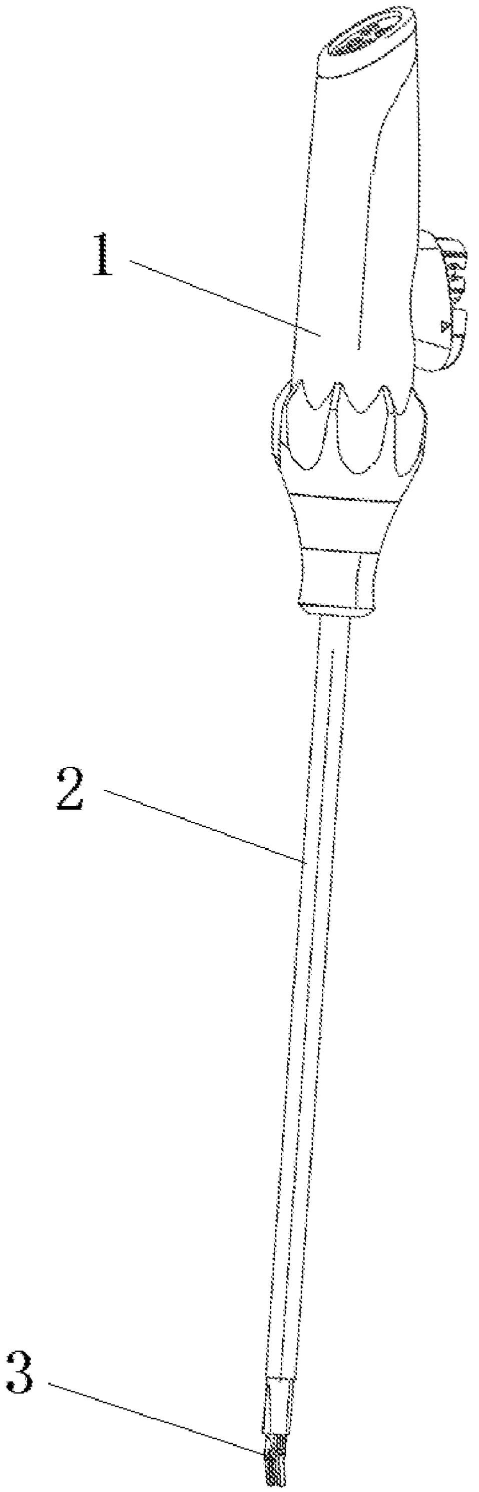
FIG. 1 is a structural schematic view of a clip applicator provided by Embodiment I.
Figure 2:
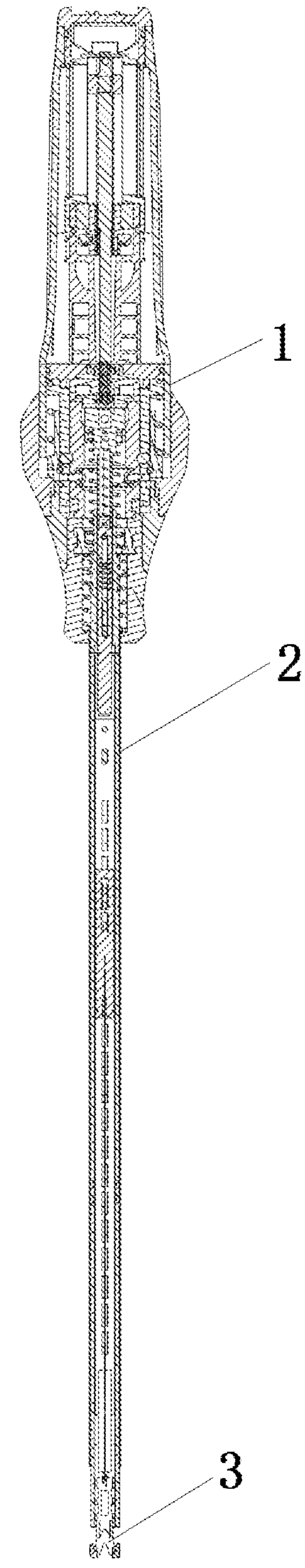
FIG. 2 is a cross-sectional schematic view of the clip applicator in FIG. 1.

- 1: adapter; 11: drive shaft; 12: second lock structure; 13: guide portion; 14: plug slot;
- 2: clip-cartridge assembly; 21: clip-cartridge shaft; 22: axial plug hole; 23: snap member; 24: release surface; 25: radial taper hole; 26: limit surface; 27: first reset member; 28: reset member; 29: clip-push mechanism; 210: second reset member; 211: tube body; 212: plug member; 213: expansion sleeve; 214: snap hole; 215: flexible tab; 216: ball head;
- 3: clip jaw.

DETAILED DESCRIPTION

In order to better explain the present disclosure and make it easier to be understood, the present disclosure will be described below in detail through specific embodiments in conjunction with the accompanying drawings. In the description of the present disclosure, the definition of "proximal" and "distal" is that: a direction from a proximal end to a distal end is a direction from a doctor to a patient when the clip applicator is used.

Embodiment I

As shown in FIG. 1 to FIG. 6, this embodiment provides a clip applicator; and the clip applicator includes an adapter 1 and a clip-cartridge assembly 2 that are detachably plugged together.

For example, the clip-cartridge assembly 2 includes a clip-cartridge shaft 21 and a tube body 211; the tube body 211 is a proximal-end outer shell of the clip-cartridge assembly 2 or a component within the proximal-end outer shell of the clip-cartridge assembly 2; the tube body 211 is an integral component or a separable component; one of functions of the tube body 211 is that an inner wall of the tube body 211 serves as a limit structure to limit a movement position of a moving component provided within the tube body 211. For example, a proximal end of the clip-cartridge shaft 21 is inserted into the tube body 211, and a reset member 28, for example, a spring, is arranged between the clip-cartridge shaft 21 and the tube body 211. In this embodiment, the reset member 28 is provided to provide an auxiliary reset force; however, in other embodiments, the reset member 28 and a structure cooperating with the reset member 28 may be omitted so that the structure of the clip applicator becomes simpler.

For example, when the adapter 1 and the clip-cartridge assembly 2 are just plugged together, the clip-cartridge shaft 21 is located at a proximal-end initial position of the clip-cartridge shaft. The proximal-end initial position of the clip-cartridge shaft for example is an extreme position of the clip-cartridge shaft 21 at the proximal end, which is limited by a block portion provided in the tube body 211; however, the proximal-end initial position of the clip-cartridge shaft 21 may be not the extreme position of the clip-cartridge shaft 21 at the proximal end but is a position where the clip-cartridge shaft 21 is in a natural state when the adapter 1 and the clip-cartridge assembly 2 are just plugged together. Because the clip-cartridge shaft 21 is in a free state when the adapter 1 and the clip-cartridge assembly 2 are just plugged together, the proximal-end initial position of the clip-cartridge shaft is not strictly limited to a fixed position, and may change in the axial direction.

For example, the adapter 1 is provided with a drive shaft 11 and a drive mechanism, the drive shaft 11 is rotatable and axially movable; the drive mechanism is connected with the drive shaft 11, and drives the drive shaft 11 to move along an axial direction of the drive shaft 11 and to rotate; and axial movement and rotation of the drive shaft 11 are independent. The drive mechanism may adopt any possible mechanism capable of implementing functions thereof. For example, the drive shaft 11 is a revolution body; and a proximal end of the drive shaft 11 is provided with an external thread. The drive mechanism includes a longitudinal movement drive electromotor/motor and a rotation drive electromotor/motor; rotation of the longitudinal movement drive electromotor/motor is transmitted to external teeth of a gear to drive the gear to rotate; internal teeth of the gear engage with the external thread of the drive shaft 11 to form a "screw-nut" transmission relationship, so that rotation of the gear is converted into forward-backward movement of the drive shaft 11 along the axis direction of the drive shaft 11. The rotation drive electromotor/motor is connected with the drive shaft 11, and drives the drive shaft 11 to rotate. Therefore, lock of the drive shaft 11 and the clip-cartridge shaft 21 is a lock allowing that the drive shaft 11 and the clip-cartridge shaft 21 are capable of synchronously moving axially and synchronously rotating. When the adapter 1 and the clip-cartridge assembly 2 are plugged together, the drive shaft 11 is located on a proximal side of the clip-cartridge shaft 21. In this embodiment, the drive shaft 11 is driven by the drive mechanism to move between a proximal-end initial position of the drive shaft, a connection position, and a distal-end terminate position of the drive shaft sequentially provided from the proximal end to the distal end.

Figure 3:
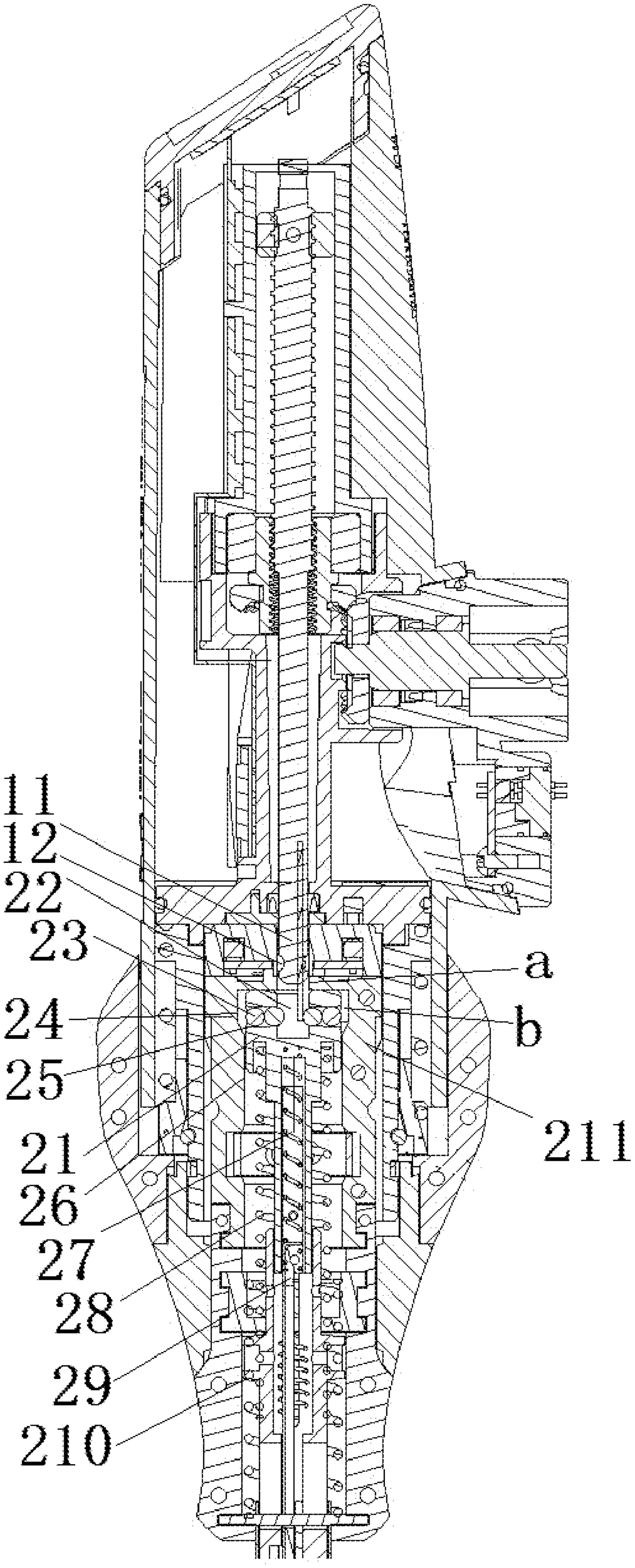
FIG. 3 is a partial cross-sectional schematic view of the clip applicator in FIG. 1, which shows that a clip-cartridge shaft is located at a proximal-end initial position of the clip-cartridge shaft and a drive shaft is located at a proximal-end initial position of the drive shaft.

Referring to FIG. 3, when the adapter 1 and the clip-cartridge assembly 2 are just plugged together, the drive shaft 11 is located at the proximal-end initial position of the drive shaft (position a in FIG. 3), the clip-cartridge shaft 21 is located at the proximal-end initial position of the clip-cartridge shaft, and at this time, the distal end of the drive shaft 11 is axially spaced apart from the proximal end of the clip-cartridge shaft 21. The proximal-end initial position of the drive shaft for example is an extreme position of the drive shaft 11 at the proximal end; however, the proximal-end initial position of the drive shaft may not be the extreme position but is a position where the drive shaft 11 in a natural state when the adapter 1 and the clip-cartridge assembly 2 are just plugged together. If the drive shaft 11 and the clip-cartridge shaft 21 are connected when the adapter 1 and the clip-cartridge assembly 2 are just plugged together, then the connection of the drive shaft 11 and the clip-cartridge shaft 21 may form a resistance force against the plugging of the adapter 1 and the clip-cartridge assembly 2; thus, in order that the adapter 1 and the clip-cartridge assembly 2 are plugged together smoothly, the drive shaft 11 and the clip-cartridge shaft 21 do not contact and are not connected with each other when the drive shaft 11 and the clip-cartridge shaft 21 are at their respective proximal-end initial positions.

Figure 4:
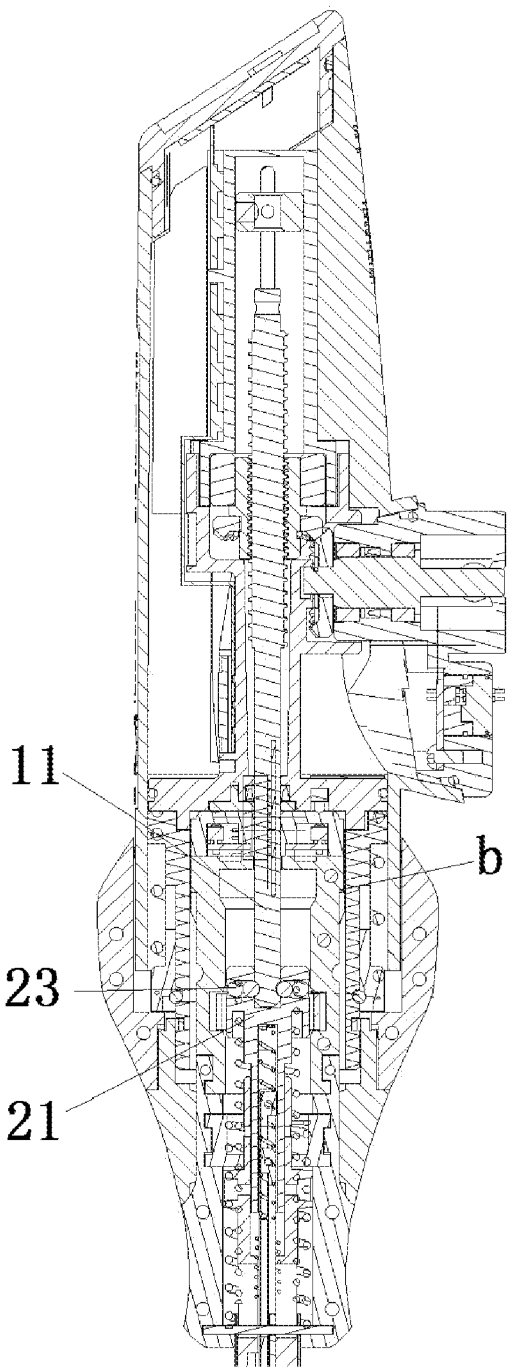
FIG. 4 is a partial cross-sectional schematic view of the clip applicator in FIG. 1, which shows that the clip-cartridge shaft is located at a certain position between the proximal-end initial position and a distal-end terminate position of the clip-cartridge shaft, and the drive shaft is located at a certain position between a connection position and a distal-end terminate position.

Referring to FIG. 3 and FIG. 4, if the clip-cartridge shaft 21 is needed to move toward the distal end, then the drive shaft 11 moves in a straight line along the distal-end direction from the proximal-end initial position of the drive shaft to the connection position (position b in FIG. 4), and is connected with the clip-cartridge shaft 21 located at the proximal-end initial position of the clip-cartridge shaft so as to achieve a connection, which is a separable connection under an axial external force, of the drive shaft 11 and the clip-cartridge shaft 21. If the adapter 1 and the clip-cartridge assembly 2 are needed to be separated from each other at the connection position, the clip-cartridge shaft 21 and the drive shaft 11 are separated by applying the clip-cartridge shaft 21 or the drive shaft 11 with an axial force, and the axial force impels the clip-cartridge shaft 21 and the drive shaft 11 to move away from each other and then separate from each other.

For example, in other embodiments, the connection position may be the proximal-end initial position of the drive shaft 11, that is, when the adapter 1 and the clip-cartridge assembly 2 are just plugged together, the drive shaft 11 and the clip-cartridge shaft 21 are connected with each other, and the connection of the drive shaft 11 and the clip-cartridge shaft 21 is the separable connection under the axial external force. This arrangement may increase the resistance force against the plugging of the adapter 1 and the clip-cartridge assembly 2, but still falls within the protection scope of the present disclosure.

Referring to FIG. 4, the drive shaft 11 continues to move in the straight line from the connection position toward the distal end, the drive shaft 11 pushes the clip-cartridge shaft 21 to leave the proximal-end initial position of the clip-cartridge shaft and move toward the distal end; when the drive shaft 11 moves to the distal-end terminate position of the drive shaft, the clip-cartridge shaft 21 moves to the distal-end terminate position of the clip-cartridge shaft. When the clip-cartridge shaft 21 is located at the distal-end terminate position of the clip-cartridge shaft or at a position between the proximal-end initial position of the clip-cartridge shaft and the distal-end terminate position of the clip-cartridge shaft, and when the drive shaft 11 is located at the distal-end terminate position of the drive shaft or at a position between the connection position and the distal-end terminate position of the drive shaft, the clip-cartridge shaft 21 and the drive shaft 11 are in a lock state, that is, the clip-cartridge shaft 21 and the drive shaft 11 are fixedly connected with each other so that the clip-cartridge shaft 21 and the drive shaft 11 are capable of synchronously moving an rotating, and the drive shaft 11 drives the clip-cartridge shaft 21 to rotate and axially move. As discussed above, the drive shaft 11 in this embodiment is rotatable and axially movable, so the lock (i.e. the fixed connection) between the drive shaft 11 and the clip-cartridge shaft 21 is a fixed connection which allows that the clip-cartridge shaft 21 and the drive shaft 11 synchronously move and rotate. If a movement mode of the drive shaft 11 in other embodiments changes, then movement defined by the lock between the drive shaft 11 and the clip-cartridge shaft 21 also changes, details of which may refer to Embodiment 3 and Embodiment 4.

Similarly, when the drive shaft 11 moves from the distal-end terminate position of the drive shaft along the proximal-end direction to the connection position, the drive shaft 11 pulls the clip-cartridge shaft 21 toward the proximal end back to the proximal-end initial position of the clip-cartridge shaft, and the lock of the drive shaft 11 and the clip-cartridge shaft 21 becomes the separable connection under the axial external force. When the drive shaft 11 continues to move toward the proximal end from the connection position or when the clip-cartridge assembly 2 is separated from the adapter 1, the drive shaft 11 and the clip-cartridge shaft 21 are axially separated for each other.

Therefore, by being driven by the drive shaft 11, the clip-cartridge shaft 21 moves between the proximal-end initial position of the clip-cartridge shaft and the distal-end terminate position of the clip-cartridge shaft. For example, the distal-end terminate position of the drive shaft 11 is not an extreme position of the drive shaft 11 at the distal end; and according to actual conditions, the distal-end terminate position of the drive shaft 11 may change, so the distal-end terminate position of the clip-cartridge shaft changes correspondingly, which will not be limited here.

To sum up, on the one hand, at the proximal-end initial position of the clip-cartridge shaft, the clip-cartridge shaft 21 and the drive shaft 11 are in the connection which is separable under the axial external force, to facilitate the pluggable connection between the adapter 1 and the clip-cartridge assembly 2; on the other hand, at positions other than the proximal-end initial position of the clip-cartridge shaft, the clip-cartridge shaft 21 and the drive shaft 11 are in the lock state, so when the clip-cartridge shaft 21 is required to reset from the distal-end terminate position of the clip-cartridge shaft to the proximal-end initial position of the clip-cartridge shaft, movement of the drive shaft 11 along the proximal-end direction directly pulls the clip-cartridge shaft 21 back to the proximal-end initial position of the clip-cartridge shaft, so that the clip-cartridge shaft 21 is stably and reliably pulled back and reset, and the problem that the clip-cartridge shaft 21 fails to fire again due to the failed reset is avoided. Meanwhile, at positions other than the initial position, the clip-cartridge assembly 2 and the adapter 1 are locked because the clip-cartridge shaft and drive shaft are locked (of course, there may be other locking mechanism between the clip-cartridge assembly and the adapter), so that the clip-cartridge assembly cannot be pulled out by error, which improves stability and safety of the clip applicator.

Referring to FIG. 3 and FIG. 4, in this embodiment, the clip-cartridge shaft 21 is provided with a first lock structure; the drive shaft 11 is provided with a second lock structure 12; and the clip-cartridge assembly 2 is provided with a lock control structure.

For example, the first lock structure includes an axial plug hole 22 and a snap member 23. The axial plug hole 22 is arranged at the proximal end of the clip-cartridge shaft 21, and the axial plug hole 22 is plugged with the distal end of the drive shaft 11. The snap member 23 moves radially to be inserted into the axial plug hole 22, and snapped with the distal end of the drive shaft. In this embodiment, the snap member 23 includes a plurality of groups of lock beads arranged around an axis of the clip-cartridge shaft 21; each group of lock beads includes two lock beads arranged along a radial direction; a hole for accommodating the lock beads of the clip-cartridge shaft 21 is a radial taper hole 25; a smaller end of the radial taper hole 25 is communicated with the axial plug hole 22, the lock bead is capable of partially passing through the smaller end of the radial taper hole. For example, the "radial direction" refers to a direction perpendicular to the axis of the clip-cartridge shaft 21, that is, a direction from a sidewall of the clip-cartridge shaft 21 to the axial plug hole 22 and perpendicular to the axial plug hole 22. Of course, the present disclosure is not limited thereto, the total number of each group of lock beads may be one, three or more than three, and the snap member 23 may be a latch, a spring piece, or any other appropriate component capable of snapping with the drive shaft.

For example, the second lock structure 12 comprises a plurality of lock grooves arranged at the distal end of the drive shaft 11 in one-to-one correspondence with the plurality of groups of lock beads, that is, the plurality of lock grooves are distributed around the axis. The plurality of groups of lock beads and the plurality of lock grooves cooperate with each other, so that the clip-cartridge shaft 21 is pulled back by the drive shaft 11 more stable and reliable. In order that the drive shaft 11 and the clip-cartridge shaft 21 synchronously rotate, an independent lock groove is provided to correspond to each group of lock beads (that is, the plurality of lock grooves are independent from each other). If the synchronous rotation of the drive shaft 11 and the clip-cartridge shaft 21 is not required, an annular lock groove is provided to cooperate with the plurality of groups of lock beads.

Meanwhile, in order to ensure a simple and convenient plugging of the adapter 1 and the clip-cartridge assembly 2 and in order to ensure correspondence between the plurality of groups of lock beads and the plurality of lock grooves when the adapter 1 and the clip-cartridge assembly 2 are plugged together (i.e., the first lock structure and the second lock structure 12 circumferentially correspond to each other), the plurality of groups of lock beads and the plurality of lock grooves are evenly arranged around the axis to reduce alignment difficulties, and further, a guide structure is arranged in the adapter 1 and the clip-cartridge assembly 2 to ensure one-to-one correspondence between the plurality of groups of lock beads and the plurality of lock grooves when the guide structure is in place.

Figure 5:
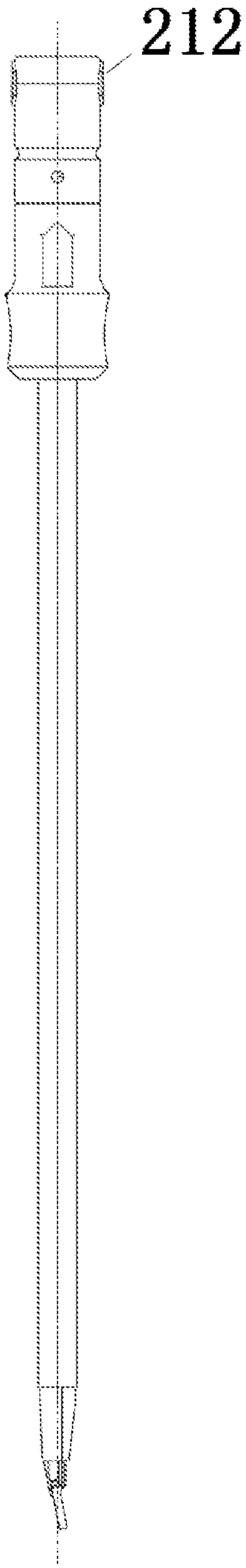
FIG. 5 is a structural schematic view of a clip-cartridge assembly of the clip applicator in FIG. 1.
Figure 6:
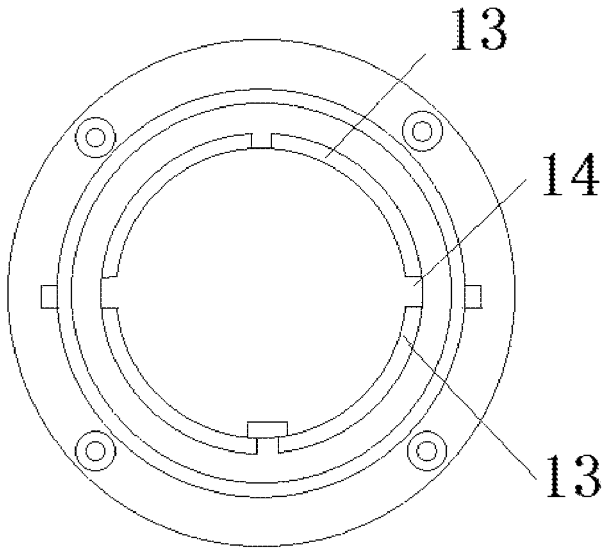
FIG. 6 is a schematic view of an end surface of an adapter of the clip applicator in FIG. 1.

For example, referring to FIG. 5 and FIG. 6, an optional implementation mode of the guide structure is that a guide portion 13 is provided on the adapter 1, so that the clip-cartridge assembly 2 is automatically guided in place during a process of being plugged into the adapter 1 while rotating.

Specifically, the guide portion 13 is a guide groove arranged on the adapter 1; the guide groove extends along a circumferential direction from a position on an end surface in the adapter 1 that faces toward the distal end and gradually increases in depth during the process of extending to be connected with a plug slot 14 of the adapter 1; an thus, as the clip-cartridge assembly 2 is plugged into the adapter 1 while rotating, the guide groove guides a plug member 212, that needs to be plugged into the plug slot 14, of the clip-cartridge assembly 2 to the plug slot 14. In order that a rotation direction of the clip-cartridge assembly 2 during the clip-cartridge assembly 2 is plugged into the adapter is not limited, two guide grooves are symmetrically arranged on both sides of the plug slot 14, and the two guide grooves gradually increase in depth during a process of extending to the plug slot 14 provided between two guide grooves. For example, a plurality of plug slots 14 are arranged, and the plurality of plug slots 14 are evenly arranged along a circumferential direction. Correspondingly, a plurality of guide portions 13 are arranged, and the plurality of guide portions 13 are arranged along the circumferential direction. Taking one plug slot 14 and two guide portions 13 on both sides of the plug slot 14 as a group, respective groups are the same and evenly arranged along the circumferential direction, which thus makes blind assembly possible, saves mounting procedures, and makes mounting easy.

The plurality of plug slots 14 are evenly arranged along the circumferential direction, and correspondingly, a plurality of plug members 212 are also evenly arranged in the clip-cartridge assembly 2 along the circumferential direction. The plug member 212 of the clip-cartridge assembly 2 is a boss; a proximal end and a distal end of the boss gradually taper to form a triangle, an arc, or a trapezoid; and such design is favorable for smooth and convenient guidance during the clip-cartridge assembly 2 is plugged into the adapter and during clip-cartridge assembly 2 is pulled out of the adapter. In this embodiment, the proximal end and the distal end of the boss are triangular, and a middle portion of the boss is rectangular, thus the boss has a double-arrow-like shape. In this way, the tapering proximal end of the boss moves in the guide groove with rotation of the clip-cartridge assembly 2 until it reaches the plug slot 14 and is plugged into the plug slot 14; and when the clip-cartridge assembly 2 is pulled out of the adapter 1, the tapering distal end provide a guidance.

In addition, for example, the plug member 212 is a plug elastically connected with the clip-cartridge assembly 2, and a deformation direction of the elastic connection is the axial direction, which thus may prevent the plug slot from being missed due to fast rotation.

To sum up, under the guidance of the guide portion 13, after the clip-cartridge assembly 2 and the adapter 1 are plugged together, the first lock structure of the clip-cartridge shaft 21 and the second lock structure 12 of the drive shaft 11 correspond with each other.

Further, the lock control structure includes a release surface 24 and a limit surface 26 located on an outer side of the clip-cartridge shaft 21; the limit surface 26 is located on a distal side of the release surface 24; and the release surface 24 and the limit surface 26 for example are portions of an inner wall of the tube body 211, or portions of an inner wall of other component provided in the tube body 211, which will not be limited here. In this embodiment, the release surface 24 is an annular surface, the limit surface 26 is also an annular surface; and a diameter of the release surface 24 is greater than a diameter of the limit surface 26. A smooth transition connection is provided between the limit surface 26 and the release surface 24; for example, a slope is provided between the limit surface 26 and the release surface 24, as shown in the drawing. The slope gradually provides an abutting pressure on the snap member during the snap member moves with the clip-cartridge shaft toward the distal end, and thus the snap member gradually locks the drive shaft. Such a gradual lock process is considered as a connection separable under the axial force when lock is insufficient to resist the force of pulling out the clip-cartridge assembly, and is considered as being locked tightly when lock is sufficient to resist the force of pulling out the clip-cartridge assembly.

When the clip-cartridge shaft 21 is located at the proximal-end initial position of the clip-cartridge shaft, the release surface 24 and the clip-cartridge shaft 21 are spaced apart from each other, and a separation distance between release surface 24 and the clip-cartridge shaft 21 is set such that the snap member 23 is capable of moving to exit the axial plug hole 22 without falling out of the radial taper hole 25, thus providing a space for the snap member 23 to move outward without limiting the snap member 23.

When the clip-cartridge shaft 21 is located at the distal-end terminate position of the clip-cartridge shaft and a position between the proximal-end initial position of the chamber shaft and the distal-end terminate position of the clip-cartridge shaft, the limit surface 26 pushes the snap member 23 to be inserted into the axial plug hole 22 and snapped with the distal end of the drive shaft 11; that is, the lock bead is partially inserted into the lock groove under the action of the limit surface 26 to lock with the lock groove.

Therefore, the lock control structure cooperates with the first lock structure and the second lock structure 12, so that the clip-cartridge shaft 21 and the drive shaft 11 form the connection separable under the axial external force at the proximal-end initial position of the clip-cartridge shaft, and so that the clip-cartridge shaft 21 is locked with the drive shaft 11 at the distal-end terminate position of the clip-cartridge shaft and at the position between the proximal-end initial position of the clip-cartridge shaft and the distal-end terminate position of the clip-cartridge shaft.

It should be understood that, in other embodiments, the release surface 24 and the limit surface 26 may be arc surfaces cooperating with the snap member 23; and a plurality of arc surfaces are provided to cooperate with the plurality of snap members 23.

For example, the first lock structure and the second lock structure 12 may have other structures.

Figure 7:
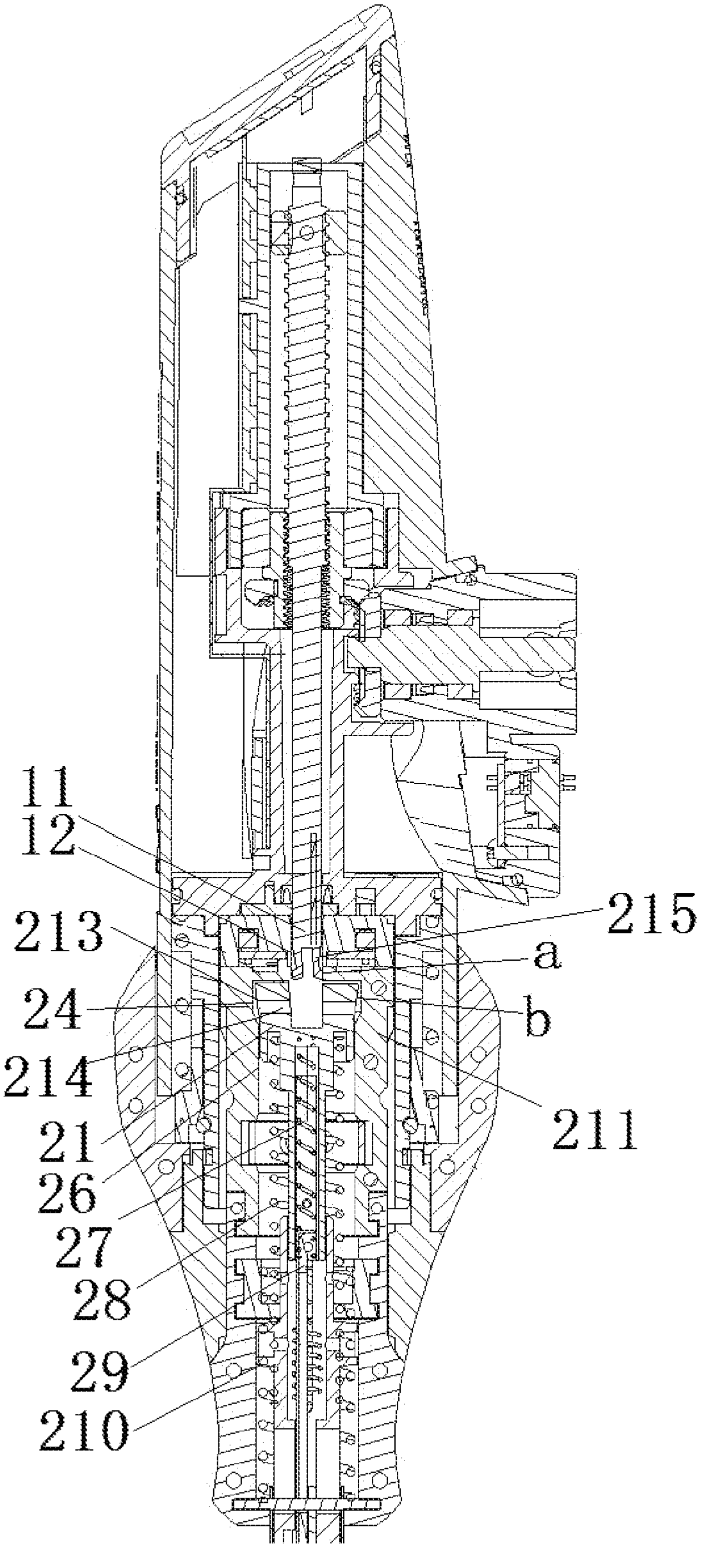
FIG. 7 shows an alternative mode of a connection structure of the clip-cartridge shaft and the drive shaft of the clip applicator in FIG. 1.

For example, referring to FIG. 7, the first lock structure is an expansion sleeve 213 provided at the proximal end of the clip-cartridge shaft, and snap holes 214 are provided in the expansion sleeve 213 along the circumferential direction; the second lock structure 12 comprises a plurality of flexible tabs 215; and the lock control structure is the same as described above. In this case, when the clip-cartridge shaft 21 is located at the proximal-end initial position of the clip-cartridge shaft, the expansion sleeve 213 expands slightly outward, and the flexible tab 215 is inserted into the snap hole of the expansion sleeve 213 because of the axial movement of the drive shaft 11. When the clip-cartridge shaft 21 moves toward the distal end, the limit surface 26 squeezes the expansion sleeve 213 inwards, so that the insertion between the expansion sleeve 213 and the flexible tab 215 is much firmer, thereby the clip-cartridge shaft 21 and the drive shaft are locked with each other.

Figure 8:
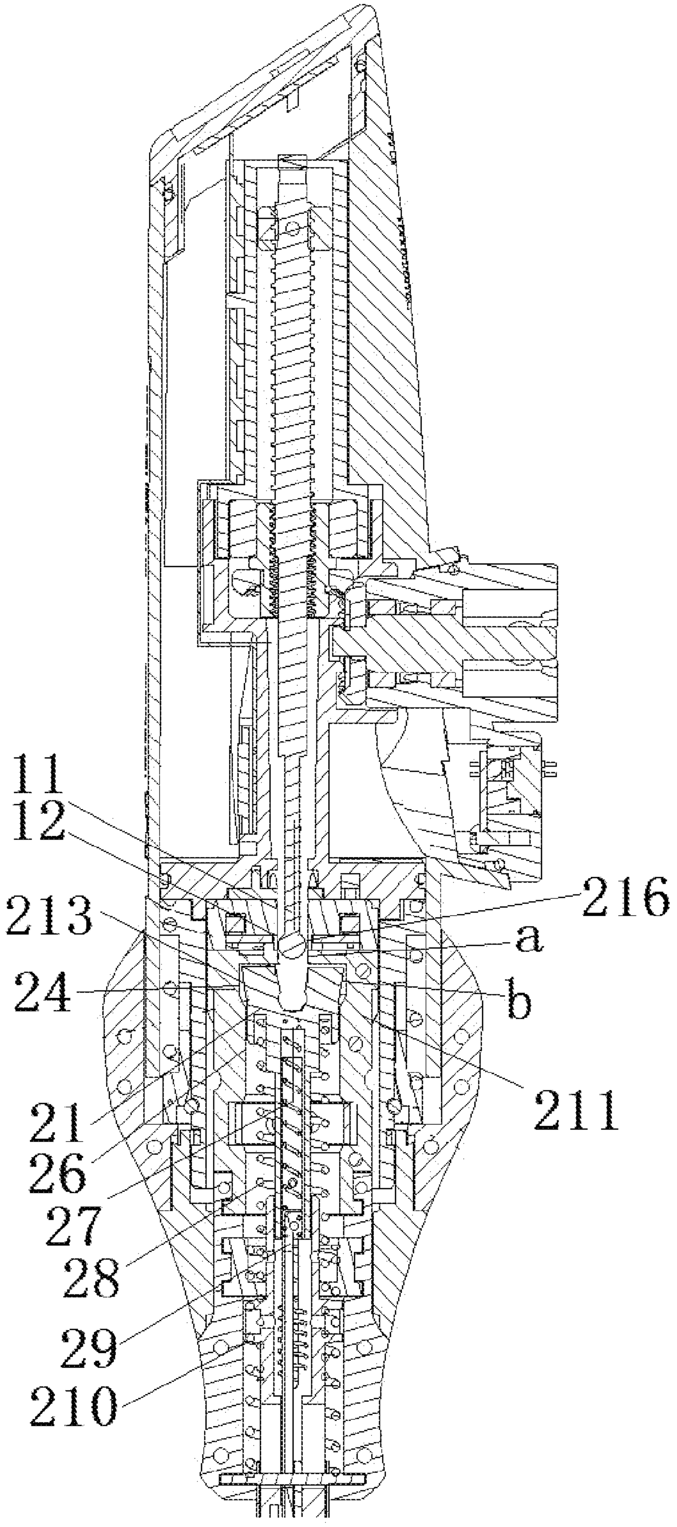
FIG. 8 shows another alternative mode of a connection structure of the clip-cartridge shaft and the drive shaft of the clip applicator in FIG. 1.

For example, as shown in FIG. 8, the first lock structure is the expansion sleeve 213 provided at the proximal end of the clip-cartridge shaft; the expansion sleeve 213 is provided with an axial plug hole 22; the axial plug hole 22 for example comprises a spherical hole and a conical hole communicated with each other; the spherical hole is located at a distal end of the conical hole and a smaller end of the conical hole is connected with the spherical hole; a diameter of the spherical hole is greater than a diameter of the smaller end of the conical hole; the second lock structure 12 is a plug portion at the distal end of the drive shaft, the plug portion has a same diameter as the drive shaft or is configured as a ball head 216; and the lock control structure is the same as described above. In this case, when the clip-cartridge shaft 21 is located at the proximal-end initial position of the clip-cartridge shaft, the expansion sleeve 213 expands slightly outward, and the ball head 216 is inserted into the axial plug hole 22 of the expansion sleeve 213, which is in a relaxed state. When the clip-cartridge shaft 21 moves toward the distal end, the limit surface 26 squeezes the expansion sleeve 213 inwards, so that insertion between the expansion sleeve 213 and the ball head 216 is much firmer, thereby the clip-cartridge shaft 21 and the drive shaft are tightly locked. An advantage of the structure is that no guide portion is needed to guide the first lock structure and the second lock structure to align with each other.

In addition, in this embodiment, the clip-cartridge assembly 2 further includes a clip-push mechanism 29, a firing mechanism, a first reset member 27 and a second reset member 210; the clip-push mechanism 29 and the firing mechanism are at least partially located in the tube body 211. The clip-push mechanism 29 is configured for feeding the clip to the clip jaw 3 provided at the distal end of the clip applicator; the firing mechanism is configured for controlling the clip jaw 3 to be closed and opened, and the clip is fired when the clip jaw 3 is closed.

During the clip-cartridge shaft 21 moves from the proximal-end initial position of the clip-cartridge shaft to the distal-end terminate position of the clip-cartridge shaft 21, the clip-cartridge shaft 21 firstly drives the clip-push mechanism 29 to move along the distal-end direction (the position where the clip-cartridge shaft 21 starts to act on the clip-push mechanism 29 is a clip feeding position) until the farthest clip at the distal end is pushed into the clip jaw 3 by the clip-push mechanism 29, and then the clip-cartridge shaft 21 drives the firing mechanism to move along the distal-end direction (the position where the clip-cartridge shaft 21 starts to act on the firing mechanism is a firing position) until the clip-cartridge shaft 21 moves to the distal-end terminate position of the clip-cartridge shaft, the clip jaw 3 is closed, and the clip is fired. To sum up, the position where the clip-cartridge shaft 21 pushes the clip-push mechanism 29 to start moving is located on a distal side of the proximal-end initial position of the clip-cartridge shaft, and the position where the clip-cartridge shaft 21 pushes the firing mechanism to start moving is located on a distal side of the position where the clip-cartridge shaft 21 pushes the clip-push mechanism 29 to start moving, and the position where the clip-cartridge shaft 21 stops driving the firing mechanism is located at the distal-end terminate position of the clip-cartridge shaft.

The first reset member 27 is arranged between the clip-push mechanism 29 and the clip-cartridge shaft 21, accumulates force during the clip-cartridge shaft 21 moves from the proximal-end initial position of the clip-cartridge shaft to the distal-end terminate position of the clip-cartridge shaft, and drives the clip-push mechanism 29 to reset during the clip-cartridge shaft 21 moves from the distal-end terminate position of the clip-cartridge shaft to the proximal-end initial position of the clip-cartridge shaft. For example, the above-described accumulated force may be a deformation force generated by compression or a deformation force generated by tension. The first reset member 27 may be a tension spring, a compression spring, a rubber member, etc.

Preferably, the clip-cartridge shaft 21 is a revolution body, and an end thereof opposite to the axial plug hole 22 is provided with an accommodation cavity; the first reset member 27 is partially located in the accommodation cavity; the clip-push mechanism 29 is connected to a cavity opening of the accommodation cavity; and the first reset member 27 is connected with the clip-push mechanism 29. One end of the clip-cartridge shaft 21 that has the axial plug hole 22 has a largest diameter, forming a groove or an end surface connected with one end of the reset member 28.

The second reset member 210 is provided between the firing mechanism and the tube body 211, or between the firing mechanism and the clip-cartridge shaft 21, accumulates force during the clip-cartridge shaft 21 moves from the proximal-end initial position of the clip-cartridge shaft to the distal-end terminate position of the clip-cartridge shaft, and drives the firing mechanism to reset during the clip-cartridge shaft 21 moves from the distal-end terminate position of the clip-cartridge shaft to the proximal-end initial position of the clip-cartridge shaft. For example, the above-described accumulated force may be a deformation force generated by compression or a deformation force generated by tension. The second reset member 210 may be a tension spring, a compression spring, a rubber member, etc.

In addition, an inductive switch for example is provided at one or more of the proximal-end initial position, the connection position, the clip feeding position, the firing position, and the distal-end terminate position, to facilitate acquiring the position of the drive shaft and/or the clip-cartridge shaft. Moreover, when a position having the inductive switch is reached, push or pullback of the drive shaft may be suspended so that the drive shaft moves discontinuously.

Embodiment II

This embodiment provides a driving method of the clip-cartridge shaft of the clip applicator according to Embodiment I, and the driving method includes a step of pushing the clip-cartridge shaft and a step of pulling back the clip-cartridge shaft.

The step of pushing the clip-cartridge shaft comprises:

S11: when the adapter 1 and the clip-cartridge assembly 2 of the clip applicator are just plugged together, the drive shaft 11 is located at the proximal-end initial position of the drive shaft, the clip-cartridge shaft 21 is located at the proximal-end initial position of the clip-cartridge shaft, and the drive shaft 11 is axially spaced apart from the clip-cartridge shaft 21. The drive mechanism drives the drive shaft 11 to move along the distal-end direction to the connection position to be connected with the clip-cartridge shaft 21 located at the proximal-end initial position of the clip-cartridge shaft, thus forming a connection separable under an axial external force of the clip-cartridge shaft 21 and the drive shaft 11.

S12: the drive mechanism continues to drive the drive shaft 11 to move toward the distal-end terminate position of the drive shaft, then the drive shaft 11 pushes the clip-cartridge shaft 21 to move from the proximal-end initial position of the clip-cartridge shaft to the distal-end terminate position of the clip-cartridge shaft ; and after the clip-cartridge shaft 21 leaves the proximal-end initial position of the clip-cartridge shaft, the drive shaft 11 and the clip-cartridge shaft 21 are locked and keep a lock state.

The step of pulling back the clip-cartridge shaft comprises:

S21: the drive shaft 11 located at the distal-end terminate position of the drive shaft drives the clip-cartridge shaft 21 located at the distal-end terminate position of the clip-cartridge shaft to move along the proximal-end direction, until the clip-cartridge shaft 21 is pulled back to the proximal-end initial position of the clip-cartridge shaft and the drive shaft 11 and the clip-cartridge shaft 21 change to be in the connection separable under the axial external force.

S22: the drive shaft 11 continues to move along the proximal-end direction and is separated from the clip-cartridge shaft 21.

To sum up, on the one hand, at the proximal-end initial position of the clip-cartridge shaft, the clip-cartridge shaft 21 and the drive shaft 11 are in the connection separable under the axial external force, to facilitate the pluggable connection between the adapter 1 and the clip-cartridge assembly 2; on the other hand, at positions other than the proximal-end initial position of the clip-cartridge shaft, the clip-cartridge shaft 21 and the drive shaft 11 are locked, so when the clip-cartridge shaft 21 is required to reset from the distal-end terminate position of the clip-cartridge shaft to the proximal-end initial position of the clip-cartridge shaft, movement of the drive shaft 11 along the proximal-end direction directly pulls the clip-cartridge shaft 21 back to the proximal-end initial position of the clip-cartridge shaft, so that the clip-cartridge shaft 21 is stably and reliably pulled back and reset, and the problem that the clip-cartridge shaft 21 fails to fire again due to the failed reset is avoided. Meanwhile, at positions other than the initial position, because the clip-cartridge shaft 21 and drive shaft 11 are locked, the clip-cartridge assembly 2 and the adapter 1 are locked by the clip-cartridge shaft 21 and drive shaft 11, so that the clip-cartridge assembly cannot be pulled out by error, which improves stability and safety of the clip applicator.

Moreover, when the adapter 1 and the clip-cartridge assembly 2 of the clip applicator are just plugged together, the clip-cartridge shaft 21 and the drive shaft 11 are still spaced apart from each, which eliminates a resistance force against the plugging of the adapter 1 and the clip-cartridge assembly 2, and makes the plugging of the adapter 1 and the clip-cartridge assembly 2 smoother. However, the present disclosure is not limited thereto; the connection position for example is the initial position of the drive shaft 11; and when the adapter 1 and the clip-cartridge assembly 2 are just plugged together, the drive shaft 11 located at the connection position and the clip-cartridge shaft 21 located at the proximal-end initial position of the clip-cartridge shaft are in the connection separable under the axial force.

Embodiment III

Main modifications of this embodiment from Embodiment I and Embodiment II are as follows:

The drive shaft 11 only moves axially under the driving of the drive mechanism moving axially, and is incapable of rotating. In this case, the lock of the drive shaft 11 and the clip-cartridge shaft 21 is a lock that allows the drive shaft 11 and the clip-cartridge shaft 21 to synchronously move axially and to rotate relative to each other. The rotation of the clip-cartridge shaft 21 for example is implemented by manually rotating other structure connected with the clip-cartridge shaft 21. For example, outer shells of the adapter 1 and the clip-cartridge assembly 2 both include rotation shells, the two rotation shells are connected, and the rotation shell of the clip-cartridge assembly is connected with the clip-cartridge shaft, so that the rotation shell of the adapter 1 is manually rotated to further drive the clip-cartridge shaft 21 to rotate. Thus, the lock between the drive shaft 21 and the clip-cartridge shaft 11 is the axial lock.

In this embodiment, in the case that the first lock structure includes the axial plug hole 22 and the snap member 23, the second lock structure 12 is an annular lock groove, and an end of the snap member of the first lock structure is an arc or is provided with a roller so that the snap member is capable of moving circumferentially in the annular lock groove, thereby the connection between the drive shaft 11 and the clip-cartridge shaft 21 that allows the drive shaft 11 and the clip-cartridge shaft 21 rotate relative to each other.

In addition, in the case that the first lock structure is the expansion sleeve 213 and the second lock structure is the ball head 216, the ball head 216 rotates relative to the expansion sleeve but the clip-cartridge shaft and the drive shaft still are locked axially by setting sizes of the ball head 216, the expansion sleeve 213, the axial hole and the limit surface.

Embodiment IV

In this embodiment, only the rotation drive mechanism is provided to drive the drive shaft 11 to rotate; in this case, the rotation of the drive shaft 11 needs to be converted into the axial movement of the clip-cartridge shaft 21. In this embodiment, a proximal end of the clip-cartridge shaft 21 is connected with a nut; a circumferential wall of the nut is provided with an external thread; the nut is screwed into a sleeve tube; an inner wall of the sleeve tube is provided with an internal thread that is screwed into the external thread. A proximal end of the sleeve tube and a distal end of the drive shaft 11 are locked so as to allow synchronous rotation of the drive shaft 11 and the sleeve tube after the adapter 1 and the clip-cartridge assembly 2 are plugged together, and the proximal end of the sleeve tube and the distal end of the drive shaft 11 are separated from each other after the adapter 1 and the clip-cartridge assembly 2 are separated from each other. Of course, the structure that converts the rotation of the drive shaft 11 into the axial movement of the clip-cartridge shaft 21 is not limited to the above structures, but may be replaced by any other structure that is capable of implementing the function.

Although the embodiments of the present disclosure have been shown and described above, it should be understood that the above-described embodiments are exemplary and cannot be understood as limitations on the present disclosure; those ordinarily skilled in the art may make changes, modifications, replacements and variations to the above-described embodiments within the scope of the present disclosure.

The invention claimed is:

1. A clip applicator, wherein the clip applicator comprises an adapter and a clip-cartridge assembly which are detachably connected together, wherein:

the clip-cartridge assembly comprises a clip-cartridge shaft that moves between a proximal-end initial position of the clip-cartridge shaft and a distal-end terminate position of the clip-cartridge shaft;

the adapter comprises a drive shaft located on a proximal side of the clip-cartridge shaft;

when the clip-cartridge shaft is located at the proximal-end initial position of the clip-cartridge shaft, the clip-cartridge shaft and the drive shaft are in a connection separable under an axial external force;

when the clip-cartridge shaft is located at the distal-end terminate position of the clip-cartridge shaft and at a position between the proximal-end initial position of the clip-cartridge shaft and the distal-end terminate position of the clip-cartridge shaft, the clip-cartridge shaft and the drive shaft are locked, wherein the clip-cartridge shaft is provided with a first lock structure, the first lock structure comprises a snap member, the snap member comprises a plurality of groups of lock beads arranged around an axis of the clip-cartridge shaft, wherein the drive shaft is provided with a second lock structure, the second lock structure comprises a plurality of lock grooves arranged at the distal end of the drive shaft in one-to-one correspondence with the plurality of groups of lock beads, wherein the clip-cartridge assembly is provided with a lock control structure;

the lock control structure cooperates with the first lock structure and the second lock structure, so that the clip-cartridge shaft and the drive shaft are in the connection separable under the axial external force at the proximal-end initial position of the clip-cartridge shaft, and so that the clip-cartridge shaft is locked with the drive shaft at the distal-end terminate position of the clip-cartridge shaft-and at the position between the proximal-end initial position of the clip-cartridge shaft and the distal-end terminate position of the clip-cartridge shaft.

2. The clip applicator according to claim 1, wherein the drive shaft moves between a proximal-end initial position of the drive shaft, a connection position, and a distal-end terminate position of the drive shaft sequentially provided from a proximal end to a distal end;

when the drive shaft is located at the proximal-end initial position of the drive shaft, the drive shaft is axially spaced apart from the clip-cartridge shaft located at the proximal-end initial position of the clip-cartridge shaft;

when the drive shaft is located at the connection position, the drive shaft and the clip-cartridge shaft located at the proximal-end initial position of the clip-cartridge shaft are in the connection separable under the axial external force; and when the drive shaft is located at the distal-end terminate position of the drive shaft, the clip-cartridge shaft is located at the distal-end terminate position of the clip-cartridge shaft.

3. The clip applicator according to claim 1, wherein the adapter comprises a drive mechanism; the drive mechanism is connected with the drive shaft and is configured for driving the drive shaft to move along an axis direction of the drive shaft and to rotate; and lock of the drive shaft and the clip-cartridge shaft is a lock that allows synchronous axial movement and synchronous rotation of the drive shaft and the clip-cartridge shaft.

4. The clip applicator according to claim 1, wherein the first lock structure further comprises an axial plug hole, the axial plug hole is provided at a proximal end of the clip-cartridge shaft, and the axial plug hole is in a pluggable connection with a distal end of the drive shaft;

the lock control structure comprises a release surface and a limit surface located on an outer side of the clip-cartridge shaft;

when the clip-cartridge shaft is located at the proximal-end initial position of the clip-cartridge shaft, the release surface and the clip-cartridge shaft are spaced apart from each other to allow a separation between the axial plug hole and the distal end of the drive shaft;

when the clip-cartridge shaft is located at the distal-end terminate position of the clip-cartridge shaft and at the position between the proximal-end initial position of the clip-cartridge shaft and the distal-end terminate position of the clip-cartridge shaft, the limit surface prevents the separation between the axial plug hole and the distal end of the drive shaft.

5. The clip applicator according to claim 4, wherein the snap member moves radially to be inserted into the axial plug hole;

when the clip-cartridge shaft is at the proximal-end initial position of the clip-cartridge shaft, a separation distance between the release surface and the clip-cartridge shaft is set such that the snap member is capable of moving to exit the axial plug hole;

when the clip-cartridge shaft is located at the distal-end terminate position of the clip-cartridge shaft and at the position between the proximal-end initial position of the clip-cartridge shaft and the distal-end terminate position of the clip-cartridge shaft, the limit surface pushes the snap member to be inserted into the axial plug hole and snapped with the distal end of the drive shaft.

6. The clip applicator according to claim 5, wherein the lock bead is partially inserted into the lock groove under an action of the limit surface so as to lock with the lock groove.

7. The clip applicator according to claim 1, wherein the clip-cartridge assembly further comprises a tube body, a clip-push mechanism, a firing mechanism, a first reset member and a second reset member; the clip-cartridge shaft, the clip-push mechanism and the firing mechanism are at least partially located in the tube body;

during the clip-cartridge shaft moves from the proximal-end initial position of the clip-cartridge shaft to the distal-end terminate position of the clip-cartridge shaft, the clip-cartridge shaft firstly drives the clip-push mechanism to move along a distal-end direction and then drives the firing mechanism to move along the distal-end direction;

the first reset member is provided between the clip-push mechanism and the clip-cartridge shaft, accumulates force during the clip-cartridge shaft moves from the proximal-end initial position of the clip-cartridge shaft to the distal-end terminate position of the clip-cartridge shaft, and drives the clip-push mechanism to reset during the clip-cartridge shaft moves from the distal-end terminate position of the clip-cartridge shaft to the proximal-end initial position of the clip-cartridge shaft;

the second reset member is provided between the firing mechanism and the tube body or the clip-cartridge shaft, accumulates force during the clip-cartridge shaft moves from the proximal-end initial position of the clip-cartridge shaft to the distal-end terminate position of the clip-cartridge shaft, and drives the firing mechanism to reset during the clip-cartridge shaft moves from the distal-end terminate position of the clip-cartridge shaft to the proximal-end initial position of the clip-cartridge shaft.

8. The clip applicator according to claim 1, wherein the adapter comprises a drive mechanism; the drive mechanism is connected with the drive shaft and is configured for driving the drive shaft to move along an axis direction of the drive shaft, and lock of the drive shaft and the clip-cartridge shaft is a lock that allows the drive shaft and the clip-cartridge shaft to synchronously move axially and to rotate relative to each other.

9. The clip applicator according to claim 1, wherein the adapter comprises a drive mechanism; the drive mechanism is connected with the drive shaft and is configured for driving the drive shaft to rotate; and lock of the drive shaft and the clip-cartridge shaft is a lock that allows a rotation of the drive shaft is converted into an axial movement of the clip-cartridge shaft.

10. A clip applicator, comprising an adapter and a clip-cartridge assembly which are detachably connected together, wherein the clip-cartridge assembly comprises a clip-cartridge shaft that moves between a proximal-end initial position of the clip-cartridge shaft and a distal-end terminate position of the clip-cartridge shaft;

the adapter comprises a drive shaft located on a proximal side of the clip-cartridge shaft;

when the clip-cartridge shaft is located at the proximal-end initial position of the clip-cartridge shaft, the clip-cartridge shaft and the drive shaft are in a connection separable under an axial external force;

when the clip-cartridge shaft is located at the distal-end terminate position of the clip-cartridge shaft and at a position between the proximal-end initial position of the clip-cartridge shaft and the distal-end terminate position of the clip-cartridge shaft, the clip-cartridge shaft and the drive shaft are locked, wherein the clip-cartridge shaft is provided with a first lock structure;

the drive shaft is provided with a second lock structure;

the clip-cartridge assembly is provided with a lock control structure;

the lock control structure cooperates with the first lock structure and the second lock structure, so that the clip-cartridge shaft and the drive shaft are in the connection separable under the axial external force at the proximal-end initial position of the clip-cartridge shaft, and so that the clip-cartridge shaft is locked with the drive shaft at the distal-end terminate position of the clip-cartridge shaft and at the position between the proximal-end initial position of the clip-cartridge shaft and the distal-end terminate position of the clip-cartridge shaft;

wherein the first lock structure further comprises an axial plug hole, the axial plug hole is provided at a proximal end of the clip-cartridge shaft, and the axial plug hole is in a pluggable connection with a distal end of the drive shaft;

the lock control structure comprises a release surface and a limit surface located on an outer side of the clip-cartridge shaft;

when the clip-cartridge shaft is located at the proximal-end initial position of the clip-cartridge shaft, the release surface and the clip-cartridge shaft are spaced apart from each other to allow a separation between the axial plug hole and the distal end of the drive shaft;

when the clip-cartridge shaft is located at the distal-end terminate position of the clip-cartridge shaft and at the position between the proximal-end initial position of the clip-cartridge shaft and the distal-end terminate position of the clip-cartridge shaft, the limit surface prevents the separation between the axial plug hole and the distal end of the drive shaft, wherein the first lock structure further comprises a snap member, the snap member moves radially to be inserted into the axial plug hole;

when the clip-cartridge shaft is at the proximal-end initial position of the clip-cartridge shaft, a separation distance between the release surface and the clip-cartridge shaft is set such that the snap member is capable of moving to exit the axial plug hole;

when the clip-cartridge shaft is located at the distal-end terminate position of the clip-cartridge shaft and at the position between the proximal-end initial position of the clip-cartridge shaft and the distal-end terminate position of the clip-cartridge shaft, the limit surface pushes the snap member to be inserted into the axial plug hole and snapped with the distal end of the drive shaft, wherein the snap member comprises a plurality of groups of lock beads arranged around an axis of the clip-cartridge shaft; each group of lock beads comprises one lock bead or a plurality of lock beads arranged along a radial direction; a hole for accommodating the lock bead of the clip-cartridge shaft is a radial taper hole; a smaller end of the radial taper hole is communicated with the axial plug hole, the lock bead is capable of partially passing through the smaller end of the radial taper hole;

the second lock structure comprises a plurality of lock grooves arranged at the distal end of the drive shaft in one-to-one correspondence with the plurality of groups of lock beads, and the lock bead is partially inserted into the lock groove under an action of the limit surface so as to lock with the lock groove.

* * * * *